US008524296B2

(12) United States Patent
Park et al.

(10) Patent No.: US 8,524,296 B2
(45) Date of Patent: Sep. 3, 2013

(54) METHOD FOR FERMENTING NATURAL MATERIALS WITH SALT AND FERMENTED EXTRACTS PREPARED THEREFROM

(75) Inventors: Jun Seong Park, Suwon-si (KR); Hye Yoon Park, Anyang-si (KR); Jin Young Lee, Yongin-si (KR); Eun Joo Kim, Suwon-si (KR); Il Young Kwak, Seoul (KR); Kyung Hee Suh, Seoul (KR); Duck Hee Kim, Seoul (KR); Han Kon Kim, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 302 days.

(21) Appl. No.: 12/919,891

(22) PCT Filed: Feb. 27, 2009

(86) PCT No.: PCT/KR2009/000935
§ 371 (c)(1),
(2), (4) Date: Aug. 27, 2010

(87) PCT Pub. No.: WO2009/107996
PCT Pub. Date: Sep. 3, 2009

(65) Prior Publication Data
US 2011/0002911 A1  Jan. 6, 2011

(30) Foreign Application Priority Data

Feb. 29, 2008 (KR) .................. 10-2008-0018970

(51) Int. Cl.
*C12G 1/00* (2006.01)
*A23B 7/00* (2006.01)
*A61K 36/00* (2006.01)

(52) U.S. Cl.
USPC ............. 426/15; 424/725; 424/736; 426/616; 426/29

(58) Field of Classification Search
None
See application file for complete search history.

(56) References Cited

FOREIGN PATENT DOCUMENTS

| JP | 11 075788 A | 3/1999 |
|---|---|---|
| JP | 2004 307709 A | 11/2004 |
| KR | 1988-0002463 | 5/1988 |
| KR | 880002463 A | 5/1988 |
| KR | 2003068870 A * | 8/2003 |
| KR | 10-2004-0065041 | 7/2004 |
| KR | 2004-0065041 | 7/2004 |
| KR | 2004-0065041 A | 7/2004 |
| KR | 20040065041 A | 7/2004 |
| WO | WO 00/60948 A1 | 10/2000 |

OTHER PUBLICATIONS

How Products Are Made (HPAM), Online, URL < http://www.madehow.com/Volume-3/Soy-Sauce.html > accessed Sep. 27, 2012, archived to Feb. 20, 2006 by the Internet Archive Wayback Machine; 6 pages.*
Search Report in EP 09 71 4198 dated Jan. 31, 2011.

(Continued)

*Primary Examiner* — Patricia Leith
(74) *Attorney, Agent, or Firm* — Nixon & Vanderhye P.C.

(57) ABSTRACT

The present invention relates to a method for fermenting natural products with salt and fermented extracts prepared thereby. The method comprises: adding a predetermined amount of salt to at least one of natural products, including medicinal herbs and cereals; naturally fermenting the salted material; and extracting the fermented salted material with a solvent. Accordingly, the method can prevent the growth of various bacteria, including putrefactive bacteria, *E. coli* and anaerobic bacteria, which are harmful to the human body, in the natural product, and it also can prevent the generation of bed smells in the natural product. The fermented extract prepared by the method has fewer side effects and is safer than fermented extracts prepared by conventional fermentation methods.

5 Claims, 2 Drawing Sheets

(56) References Cited

OTHER PUBLICATIONS

International Food Information Service (IFIS), Frankfurt-Main, DE; "Process for producing alcoholic, aqueous and oily extracts from vegetable matter by biological means. (translated) TIOL—Verfahren zur Herstellung von alkoholischen, waessrigen und oeligen Extrakten aus pflanlichem Material auf biologische Wege.", Database accession No. FS1973-09-H-1369 & DE 2 117 A 1972 (English Abstract).

Thomson Scientific, London, GB, AN 2005-735225; CN 1 623 433 A (Wang L) June 8, 2005 (English abstract).

International Search Report for PCT/KR2009/000935, mailed Oct. 9, 2009.

Office Action with English translation in CN 200980106765.0 dated May 10, 2012.

May 10, 2012 Chinese Office Action and English translation in CN200980106765.0.

* cited by examiner

P. aeruginosa     E. coli     S. aureus

METHOD FOR FERMENTING NATURAL MATERIALS WITH SALT AND FERMENTED EXTRACTS PREPARED THEREFROM

This application is the U.S. national phase of International Application No. PCT/KR2009/000935, filed 27 Feb. 2009, which designated the U.S. and claims priority to Korean Patent Application No. 10-2008-0018970, filed 29 Feb. 2008, the entire contents of each of which are hereby incorporated by reference.

TECHNICAL FIELD

The present invention relates to a method for fermenting natural products with salt and fermented extracts prepared thereby, and more particularly, to a method for fermenting at least one of natural products, including medicinal herbs and cereals, the method comprising: adding a predetermined amount of salt to the natural product; naturally fermenting the salted material; and extracting the fermented material with a solvent, and to a fermented extract prepared thereby. Accordingly, the method of the present invention can prevent the growth of various bacteria, including putrefactive bacteria, *E. coli* and anaerobic bacteria, which are harmful to the human body, in the natural product, and it also can prevent the generation of bed smells in the natural product. The fermented extract prepared by the method of the present invention has fewer side effects and is safer than fermented extracts prepared by conventional fermentation methods.

BACKGROUND ART

Recently, as interest in traditional fermented foods has increased, methods for preparing various extracts using fermentation techniques have been developed. Accordingly, functional foods, functional cosmetic products and the like produced using fermented medical herb extracts having better performance than that of unprocessed medicinal herbs have been developed.

In the prior art, methods of fermenting medicinal herbs by microorganisms were adopted. For example, Korean Patent Registration No. 10-0319377 discloses a method of fermenting vegetables and medicinal herb juice using *Lactobacillus plantarum* ATCC 11542. Also, Korean Patent Registration No. 10-0465261 discloses a method comprising preparing a medicinal herb extract from a medicinal herb mixture that contains *Astragalus* and *Lycium Chinense* fruit, adding a *Lactobacillus bulgaricus* culture to the extract, and then culturing the extract.

With the recent trend toward healthy lifestyles, the demand for methods of fermenting medicinal herbs using natural fermentation methods without using artificial factors has increased, and the demand for products produced using the fermented medicinal herbs continues to increase. However, these natural fermentation methods are difficult to use in actual products, due to the risk of spoilage and contamination caused by *E. coli*, anaerobic bacteria and the like that are harmful to the human body. In an attempt to solve such problems, a method of carrying out sterilization prior to fermentation, such as a boiling method, was developed. In this case, however, active ingredients can be degraded by heat. Thus, there is a need to develop a fermentation method that uses a non-sterilization method.

DISCLOSURE

Technical Problem

The present inventors have studied to find a natural fermentation method that overcomes the above-described problems occurring in the prior fermentation method, and, as a result, have found that the risk of spoilage and contamination occurring in the conventional natural fermentation method can be solved by a fermentation method including salting natural products such as medicinal herbs and fermenting the salted natural products, thereby completing the present invention.

Therefore, it is an object of the present invention to provide a method for fermenting natural products, which can prevent the natural products from spoilage and contamination, and fermented extracts prepared thereby.

Technical Solution

To achieve the above object, the present invention provides a method for fermenting at least one of natural products, including medicinal herbs and cereals, the method including the steps of: 1) adding a predetermined amount of salt to the natural product and naturally fermenting the salted natural product for a long period of time; and 2) extracting the fermented natural product with water or an organic solvent, thereby obtaining a salt-fermented extract.

The present invention also provides a salt-fermented extract obtained by the above-described method.

Advantageous Effects

The method for fermenting natural products with salt according to the present invention is a non-sterilization method which can prevent degradation of active ingredients in the natural products and prevent degradation and contamination caused by *E. coli* or anaerobic bacteria that are harmful to the human body. A fermented extract prepared by the above method may be used as an active ingredient for health foods and skin external preparations.

BEST MODE

Figure 1:
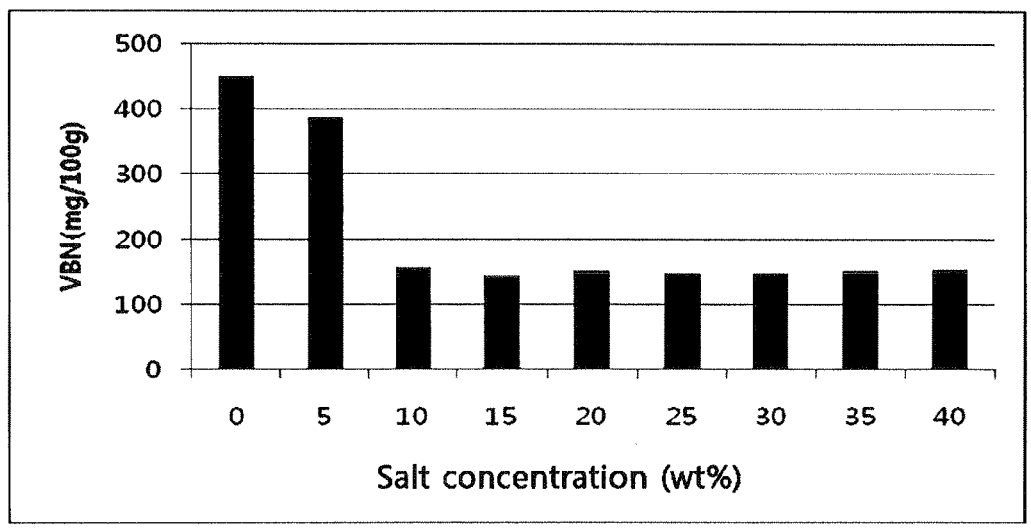
FIG. 1 is a graphic diagram showing the results of measuring the volatile basic nitrogen content of each test sample.

Hereinafter, the present invention will be described in further detail.

The present invention relates to a method for fermenting at least one of natural products, including medicinal herbs and cereals, the method including the steps of: 1) adding a predetermined amount of salt to the natural product and naturally fermenting the salted natural product for a long period of time; and 2) extracting the fermented natural product with water or an organic solvent, thereby obtaining a salt-fermented extract.

Preferred examples of salt that is used in step 1) of the inventive method include purified sodium chloride, solar salt, rock salt and bamboo salt, and the concentration of salt used in step 1) is preferably 10-30 wt % based on the total weight of the fermented natural product. If the content of salt is less than 10 wt %, it will be difficult to obtain the desired salting effect, and if the content exceeds 30 wt %, the increase in the amount of salt used will not provide a significant increase in the salting effect.

The fermentation process in the present invention may be performed at a temperature between 4° C. and 40° C. for a period ranging from 30 days to 1 year, and preferably from 6 months to 1 year, such that sufficient fermentation can occur. If the fermentation temperature is lower than 4° C., useful microorganisms will not grow well, and if the fermentation temperature is higher than 40° C., microorganisms will excessively grow to adversely affect the performance of medicinal herbs.

Also, examples of natural products to which the fermentation method of the present invention may be applied include, but are not limited to, medicinal herbs, including *Citrus junos* fruit, *Astragalus*, safflower, angelica, ginger, *Platycodon grandiflorum*, and *Poncirus trifoliata* fruit; and cereals, including soybean, rice, barley, and wheat.

The organic solvent that is used in step 2) of the method according to the present invention may be one or a mixture of two or more selected from the group consisting of purified water, methanol, ethanol, glycerin, ethyl acetate, butylene glycol, propylene glycol, dichloromethane and hexane. The extraction of step 2) is preferably carried out at a temperature between 10° C. and 80° C. for 6-24 hours. If the extraction temperature and the extraction time are out of the above-specified ranges, the extraction efficiency can be reduced or the components of the extract can be changed.

After carrying out step 2) of the method according to the present invention, the extract can be subjected to cold-water extraction at room temperature, heating and filtration according to a conventional method known in the art, thus obtaining a liquid-phase material. Alternatively, solvent evaporation, spray drying or freeze drying may additionally be carried out, thus preparing a salt-fermented extract of the natural product.

The salt-fermented extract according to the present invention is not limited to any particular application and may be used in, for example, health food additives, cosmetic compositions and pharmaceutical compositions.

MODE FOR INVENTION

Hereinafter, the present invention will be described in further detail by way of examples and test examples with reference to the accompanying drawings. Theses examples are merely proposed to understand the disclosure of the present invention, and the scope of the present invention is not limited thereto. It will be understood by those skilled in the art that variations, substitutions and insertions which are commonly well-known can be made to the present invention without departing from the spirit and scope of the appended claims.

Test Example 1

Test I for Determining the Optimal Salt Concentration of Salt-Fermented Extract 1 kg of washed *Citrus junos* fruit was mixed with each of salt solutions having various salt concentrations of 0-40 wt % and placed in pottery. Then, each of the mixtures was fermented at 4° C. for 30 days. Subsequently, 5 l of an 80% ethanol aqueous solution was added thereto, and each of the resulting solutions was extracted three times under reflux, and then settled at 15° C. for 1 day. Then, each of the solutions was filtered through filter cloth and centrifuged into residue and a filtrate. Each of the separated filtrates was concentrated under reduced pressure, thus obtaining extract samples. In order to determine the optimal salt concentration, the volatile basic nitrogen (VBN) content of each sample was analyzed. The determination of volatile basic nitrogen enables the degree of food spoilage to be understood by determining the amount of volatile basic nitrogen that is generated by protein degradation and causes a bad taste and odor, and it can estimate the degree of generation of an offensive odor resulting from spoilage in marine products such as fishes. For this purpose, about 5 g of each of the extracts was placed in a centrifugal tube, and 25 ml of distilled water and 5 ml of 20% TCA were added thereto. Each of the resulting solutions was centrifuged at 3,000 rpm for 20 minutes. Each of the supernatants was filtered and then adjusted to a volume of 50 ml by adding 2% TCA, thus obtaining test samples. 1 ml of a boric acid absorbent was placed in the inner chamber of a Conway unit, 1 ml of saturated $K_2CO_3$ and 1 ml of each sample were placed in the outer chamber, and then immediately, the chambers were covered with lids which were fixed with clips. The Conway unit was rotated while it was inclined forward/backward and left/right, so that the sample and the saturated $K_2CO_3$ solution in the outer chamber were well mixed. The mixture in the outer chamber was allowed to stand at 30° C. for 2 hours and titrated with 0.1N HCl, and the VBN content of the mixture was measured. The measurement results are shown in FIG. 1.

As can be seen from the results in FIG. 1, when the salt concentration was lower than 10 wt %, the VBN content was increased due to the spoilage of the fermented extract, whereas, when the salt concentration was higher than 10 wt %, a suitable VBN content was maintained, and thus the fermented extract was kept without spoilage.

Test Example 2

Test II (DPPH Test) for Determining the Optimal Salt Concentration of Salt-Fermented Extract In order to determine the optimal salt concentration of a salt-fermented extract, the DPPH (1,1-diphenyl-2-picryl hydrazyl) oxidation inhibitory effects of extracts prepared to have salt concentrations of 0-40 wt % in the same manner as in Test Example 1 were measured. Namely, the antioxidant activities of the extracts were evaluated by measuring the change in absorbance resulting from the reduction of the organic radical DPPH due to the oxidation of the antioxidant. The degree to which absorbance was reduced due to the inhibition of DPPH oxidation by each of the extracts was measured and compared to that of a control group, and a concentration showing an absorbance 50% lower than the absorbance of the control group was evaluated as an effective antioxidant concentration.

Figure 2:
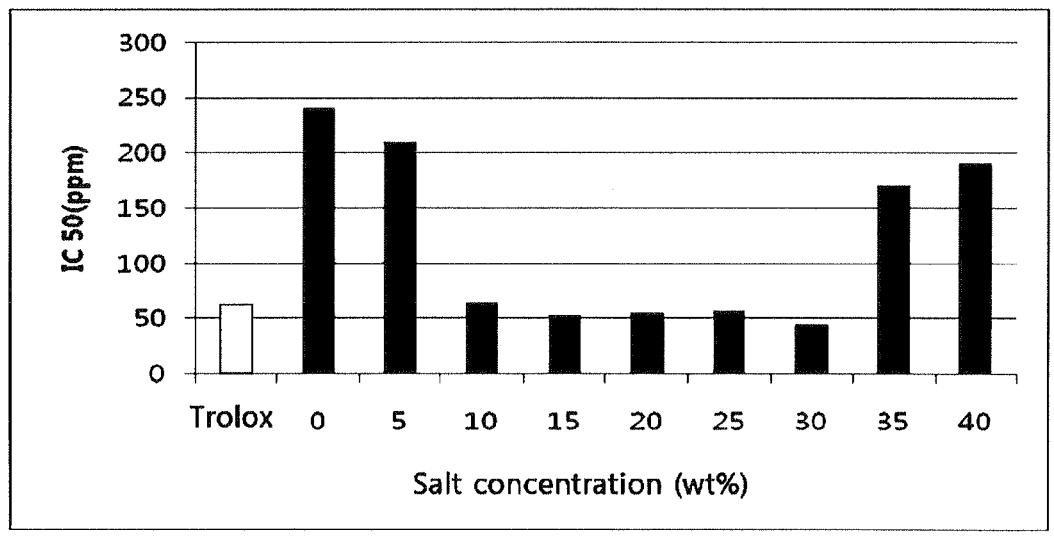
FIG. 2 is a graphic diagram showing the results of measuring the DPPH oxidation inhibitory effect of each test sample.

190 μl of a solution of 100 μM DPPH in ethanol was mixed with 10 μl of each of a control sample and the extract samples of various salt concentrations to prepare reaction solutions. Each reaction solution was allowed to react at 37° C. for 30 minutes and measured for absorbance at 540 nm. As the control sample, Trolox, a widely used synthetic antioxidant, was used. The results of DPPH analysis for each material are shown in FIG. 2. In FIG. 2, $IC_{50}$ indicates the sample concentration at which absorbance was reduced by 50% due to the added sample.

As can be seen from the results in FIG. 2, the extract samples having a salt concentration lower than 10 wt % did not show a significant antioxidant effect, whereas the extract samples having a salt concentration higher than 10 wt % showed a significantly increased antioxidant effect. However, in the extract samples having a salt concentration higher than 30 wt %, the antioxidant effect that has increased in proportion to the salt concentration was reduced rather than increased. Based on these results, the optimal salt concentration in the preparation of salt-fermented extracts according to the present invention was determined to be 10-30 wt %.

Example 1

Preparation of Salt-Fermented Extract of *Citrus Junos* Fruit 1 kg of washed *Citrus junos* fruit was mixed with a salt solution having a salt concentration of 10 wt % and placed in pottery. Then, the mixture was fermented at 4° C. for about 30 days. Subsequently, 5 l of an 80% ethanol aqueous solution was added thereto, and the resulting solution was extracted three times under reflux, and then settled at 15° C. for 1 day. The settled solution was filtered through filter cloth and centrifuged into residue and a filtrate, and the separated filtrate was concentrated under reduced pressure. The concentrated filtrate was suspended in water, the suspension was extracted five times with 1 l of ether to remove pigments, and the aqueous layer was extracted three times with 500 ml of 1-butanol. The resulting total 1-butanol layer was concentrated under reduced pressure to obtain a 1-butanol extract, which was then dissolved in a small amount of methanol. The solution was added to a large amount of ethyl acetate, and the produced precipitate was dried, thus obtaining 200 g of a salt-fermented extract of *Citrus junos* fruit.

Example 2

Preparation of Salt-Fermented Extract of *Poncirus Trifoliata* Fruit 1 kg of dried *Poncirus trifoliata* fruit was prepared and extracted in the same manner as described in Example 1, thus obtaining 150 g of a salt-fermented extract of *Poncirus trifoliata* fruit.

Comparative Example 1

Preparation of Fermented Extract *Citrus Junos* Fruit 1 kg of washed *Citrus junos* fruit was mixed with ionized water and placed in pottery. Then, the mixture was fermented at 4° C. for about 30 days. Subsequently, 5 l of an 80% ethanol aqueous solution was added thereto, and the resulting solution was extracted three times under reflux, and then settled at 15° C. for 1 day. The settled solution was filtered through filter cloth and centrifuged into residue and a filtrate, and the separated filtrate was concentrated under reduced pressure. The concentrated filtrate was suspended in water, the suspension was extracted five times with 1 l of ether to remove pigments, and the aqueous layer was extracted three times with 500 ml, of 1-butanol. The resulting total 1-butanol layer was concentrated under reduced pressure to obtain a 1-butanol extract, which was then dissolved in a small amount of methanol. The solution was added to a large amount of ethyl acetate, and the produced precipitate was dried, thus obtaining 170 g of a fermented extract of *Citrus junos* fruit.

Comparative Example 2

Preparation of Fermented Extract of *Poncirus Trifoliata* Fruit 1 kg of dried *Poncirus trifoliata* fruit was extracted in the same manner as described in Comparative Example 1, thus obtaining 195 g of a fermented extract of *Poncirus trifoliata* fruit.

Test Example 3

Test for Inhibition of Production of Harmful Bacteria

Letheen agar was poured into a Schale and solidified therein to form a primary medium. Then, each of pre-cultured *Escherichia coli* ATCC 8739, *Pseudomonas aeruginosa* ATCC 9027 and *Staphylococcus aureus* ATCC 6538 was diluted to a cell concentration of $10^5$ cells/g in Letheen agar kept at about 40° C., and each dilution was poured onto the primary medium and solidified thereon. About 0.02 ml of each of solar salt solutions having salt concentrations of 10%, 20% and 30% was applied to a sterile paper disk which was then placed on the medium having the bacterial cells spread thereon. Next, each solar salt solution was allowed to spread sufficiently at room temperature for 24 hours, and then the media were incubated at 32° C. for the optimum time. Then, whether a clear inhibition zone was formed on the Schale was observed, and the results are shown in FIG. 3.

Figure 3:
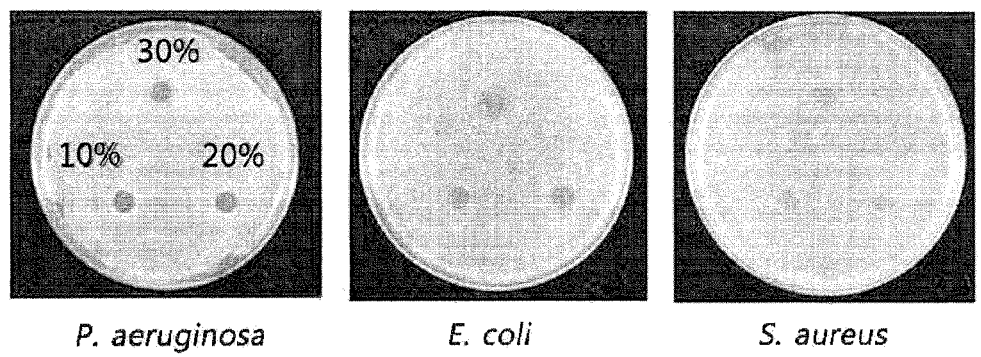
FIG. 3 shows the results of determining whether a clear inhibition zone is produced during the culture of each of *Escherichia coli* ATCC 8739, *Pseudomonas aeruginosa* ATCC 9027 and *Staphylococcus aureus* ATCC 6538 in the presence of a solar salt solution, in order to examine the influence of salt on the growth of harmful microorganisms.

As can be seen from the results in FIG. 3, salt inhibited the growth of harmful microorganisms.

Figure 4:
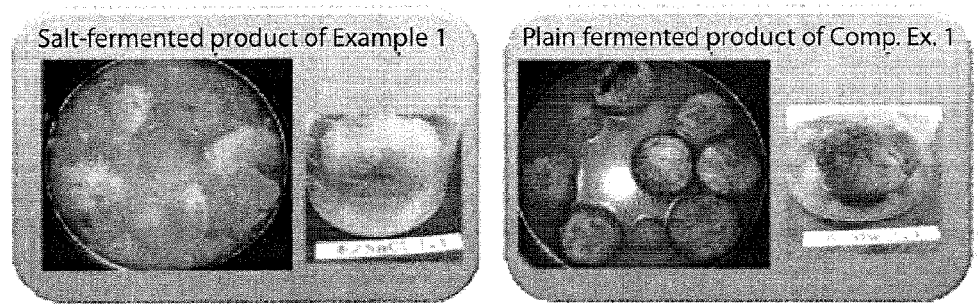
FIG. 4 is a set of photographs showing the results of observing fermented materials of Example 1 and Comparative Example 1 prior to extraction.

In addition, the results of observing the fermented products of Example 1 and Comparative Example 1 prior to extraction are shown in FIG. 4. As can be seen therein, the fermented product of Example 1 maintained the distinct yellow color of *Citrus junos* fruit, but the fermented product of Comparative Example 1 was turned green due to the growth of fungi. Moreover, in the salt-fermented product of *Citrus junos* fruit of Example 1, the characteristic fragrance of *Citrus junos* fruit remained, but the plain fermented product of Comparative Example 1 was spoiled to smell bad.

Test Example 4

Evaluation of Skin Irritation of Salt-Fermented Extract

Each of a vehicle and the extracts prepared in Examples 1 and 2 and Comparative Examples 1 and 2 was applied to the skin of New Zealand white rabbits twice a day for 4 days. After the application, the score of erythema and crust formation and the score of edema were cumulated to determine the cumulative irritation index of each test sample. The cumulative irritation index was evaluated according to the criteria shown in Table 1 below, and the evaluation results are shown in Table 2 below. The irritation index shown in Table 2 was determined according to Primary Irritation Index (P.I.I) of Draize, which is generally frequently used (Draize, J. H., Appraisal of the safety of chemical in foods, drugs and cosmetics).

TABLE 1

| | Degree of skin irritation | Score |
|---|---|---|
| Erythema and crust formation | No erythema | 0 |
| | Very weak degree of erythema (extent of barely recognizing with the naked eye) | 1 |
| | Clear erythema | 2 |
| | High degree of severity of erythema | 3 |
| | Deep crimson erythema and crust formation | 4 |
| Edema formation | No edema | 0 |
| | Very weak degree of edema (extent of barely recognizing with the naked eye) | 1 |
| | Clear edema (clearly distinguished from the surroundings) | 2 |
| | High degree of severity of edema (extent of skin's being swollen by about 1 mm) | 3 |
| | Strong degree of edema (extent of skin's being swollen by more than 1 mm and extended up to the exposed part) | 4 |

[] Primary irritation index = (average of the sum of erythema score and edema score/4)

TABLE 2

| | Primary irritation index (0-4) |
|---|---|
| Vehicle | 0.5 |
| Example 1 | 0.6 |
| Example 2 | 0.7 |
| Comp. Ex. 1 | 1.4 |
| Comp. Ex. 2 | 1.8 |

As can be seen from the results in Table 2 above, the degrees of skin irritation of the salt-fermented extracts prepared using the non-sterilization method according to the present invention were significantly reduced compared to those of the vehicle and the plain fermented extracts of Comparative Examples 1 and 2 prepared using the sterilization method.

The invention claimed is:

1. A method for fermenting at least one fruit selected from the group consisting of *Citrus junos* fruit or *Poncirus trifoliata* fruit, the method comprising the steps of:
  1) adding a predetermined amount of salt to the fruit and naturally fermenting the salted fruit for 30 days to one year; and
  2) extracting the fermented fruit with water or an organic solvent, thereby obtaining a salt-fermented extract.

2. The method of claim 1, wherein the salt used in step 1) is one selected from the group consisting of purified sodium chloride, solar salt, rock salt and bamboo salt.

3. The method of claim 1, wherein the salt used in step 1) is used in an amount of 10-30 wt % of the salt based on the total weight of the fermented fruit.

4. The method of claim 1, wherein the fermented fruit is extracted in step 2) with an organic solvent which is one or a mixture of two or more solvents selected from the group consisting of methanol, ethanol, glycerin, ethyl acetate, butylene glycol, propylene glycol, dichloromethane and hexane.

5. The method of claim 1, wherein the salted fruit is fermented in step 1) at 4-40° C.

* * * * *